(12) United States Patent
Shapeton et al.

(10) Patent No.: US 6,960,200 B2
(45) Date of Patent: *Nov. 1, 2005

(54) PACKAGE FOR REMOVABLE DEVICE TIPS

(75) Inventors: Mark Shapeton, Chestnut Hill, MA (US); Wayne Johnson, Whitman, MA (US); Michael J. Crocetta, Jr., Santa Barbara, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 217 days.

This patent is subject to a terminal disclaimer.

(21) Appl. No.: 10/201,560

(22) Filed: Jul. 23, 2002

(65) Prior Publication Data

US 2003/0014040 A1 Jan. 16, 2003

Related U.S. Application Data

(60) Division of application No. 09/661,892, filed on Sep. 14, 2000, now Pat. No. 6,478,030, which is a division of application No. 09/126,699, filed on Jul. 30, 1998, now Pat. No. 6,183,467, which is a continuation-in-part of application No. 08/709,181, filed on Sep. 6, 1996, now Pat. No. 5,814,043.

(51) Int. Cl.[7] ............................................. A61B 17/00
(52) U.S. Cl. ............................. 606/1; 606/45; 206/363; 30/329
(58) Field of Search .............................. 206/349, 352, 206/354–360, 363–370; 606/1, 41, 45; 30/329, 335

(56) References Cited

U.S. PATENT DOCUMENTS

| | | | |
|---|---|---|---|
| 3,785,051 A | | 1/1974 | Dawldowicz et al. |
| 4,173,285 A | * | 11/1979 | Kiraly et al. ............... 206/356 |
| 4,548,207 A | | 10/1985 | Reimels |
| 4,732,149 A | | 3/1988 | Sutter |
| 4,823,791 A | | 4/1989 | D'Amelio et al. |
| 4,836,201 A | | 6/1989 | Patton et al. |
| 4,850,353 A | | 7/1989 | Stasz et al. |
| 4,890,610 A | | 1/1990 | Kirwan, Sr. et al. |
| 4,960,419 A | | 10/1990 | Rosenberg |
| 4,985,034 A | * | 1/1991 | Lipton ......................... 606/167 |
| 5,009,656 A | | 4/1991 | Reimels |
| 5,089,002 A | | 2/1992 | Kirwan, Jr. |
| 5,125,927 A | | 6/1992 | Belanger |
| 5,267,998 A | | 12/1993 | Hagen |
| 5,290,285 A | | 3/1994 | Kirwan, Jr. |
| 5,346,491 A | | 9/1994 | Oertli |
| 5,361,902 A | * | 11/1994 | Abidin et al. ............... 206/370 |
| 5,571,100 A | | 11/1996 | Goble et al. |
| 5,814,043 A | | 9/1998 | Shapeton |
| 6,183,467 B1 | | 2/2001 | Shapeton |
| 6,311,838 B1 | * | 11/2001 | Johnson et al. ............. 206/363 |
| 6,358,241 B1 | | 3/2002 | Shapeton et al. |
| 6,478,030 B1 | | 11/2002 | Shapeton |

OTHER PUBLICATIONS

The Kloti Method, "High Frequency Capsulotomy," Instructions for Use and Operation, Oertli, Switzerland.

Mentor Ophthalmics, Orca™ Surgical Products, Irrigation cannula hydrodissector device tip and packaging (Oct. 1996).

Becton Dickinson & Cop., B–D 16G1 PrecisionGlide Needle, No. 5197, and packaging—prior art Look, Inc., 1–1 4" Peribulber 32mm Atkinson Point device tip and packaging (Aug. 1995).

* cited by examiner

Primary Examiner—Michael Peffley

(57) ABSTRACT

A package for a tip, such as a replaceable tip for a bipolar electrosurgical device, is used for insertion of the tip onto and removal of the tip from the end of a device handle, without requiring any direct contact between the user's hand and the tip. The package includes a housing having a tip cavity shaped to receive the tip and an opening through which the end of the handle is insertable for removable attachment to the tip. A releasable locking mechanism, which is releasable in response to the end of the handle being disposed in the opening for removable attachment to the tip, retains the tip in the tip cavity. The package may be made from a single piece of molded material, such as a clear plastic. The package may also be used with monopolar, diathermized and non-bipolar tips, as well as other sharp tips such as cannulae, pics and blades, that are attachable to the end of a handle.

26 Claims, 13 Drawing Sheets

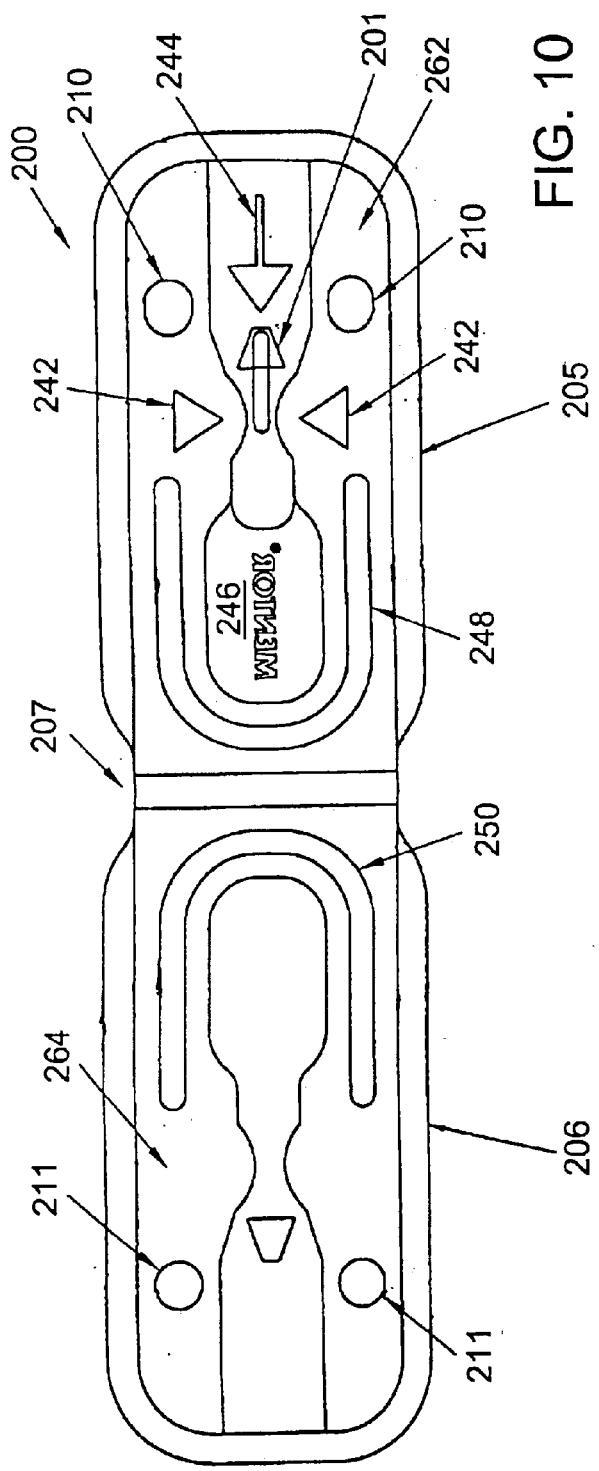
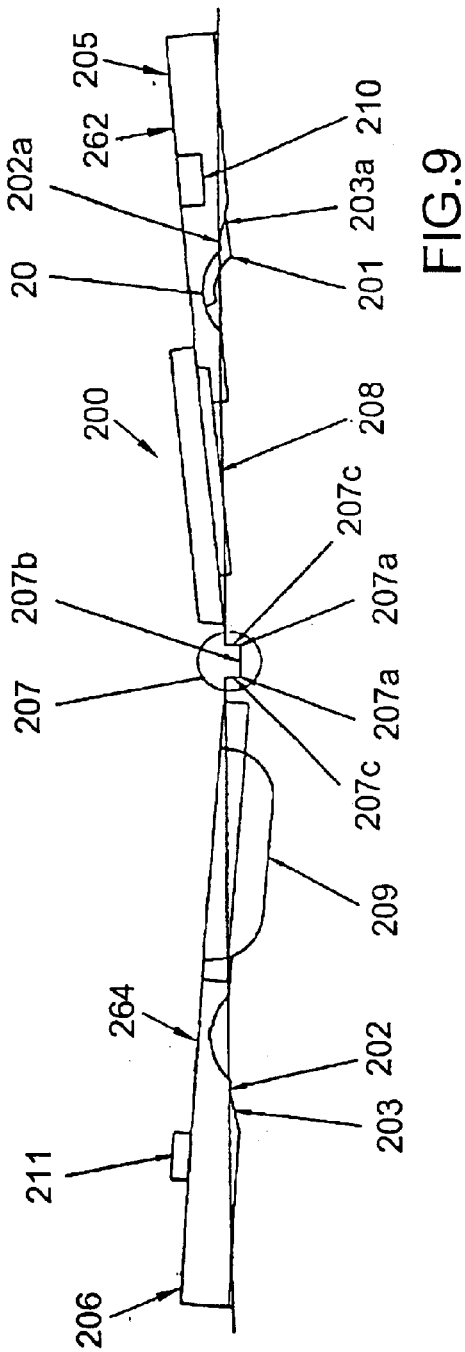

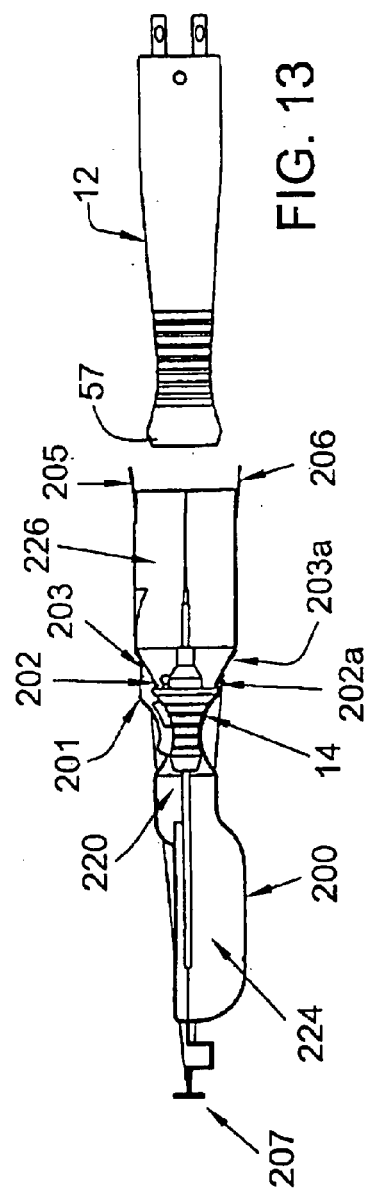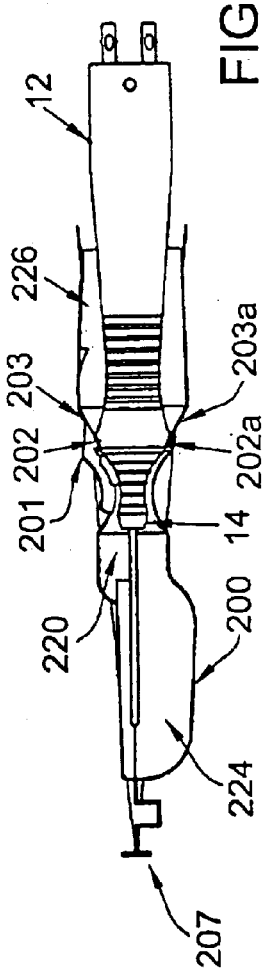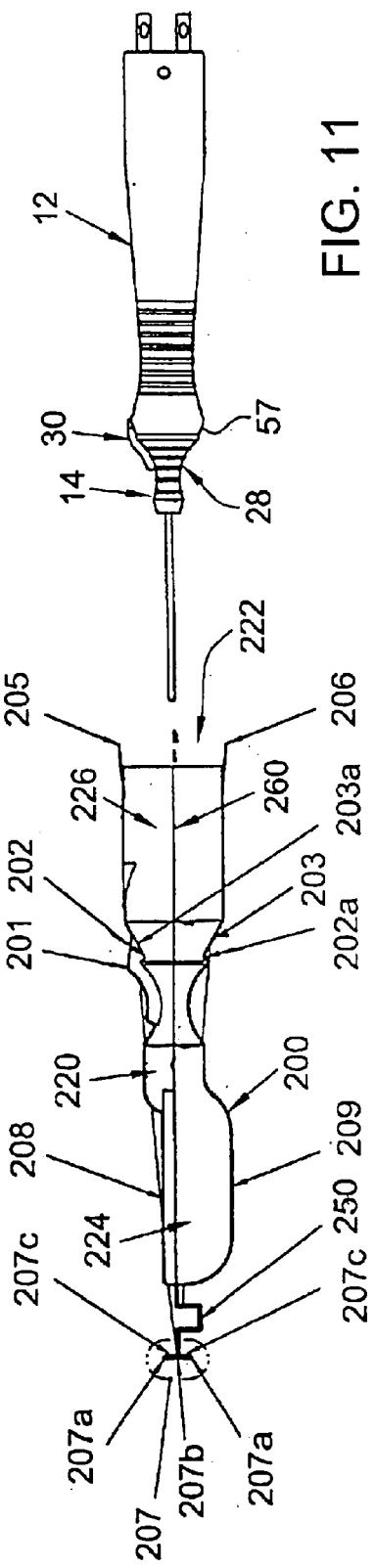

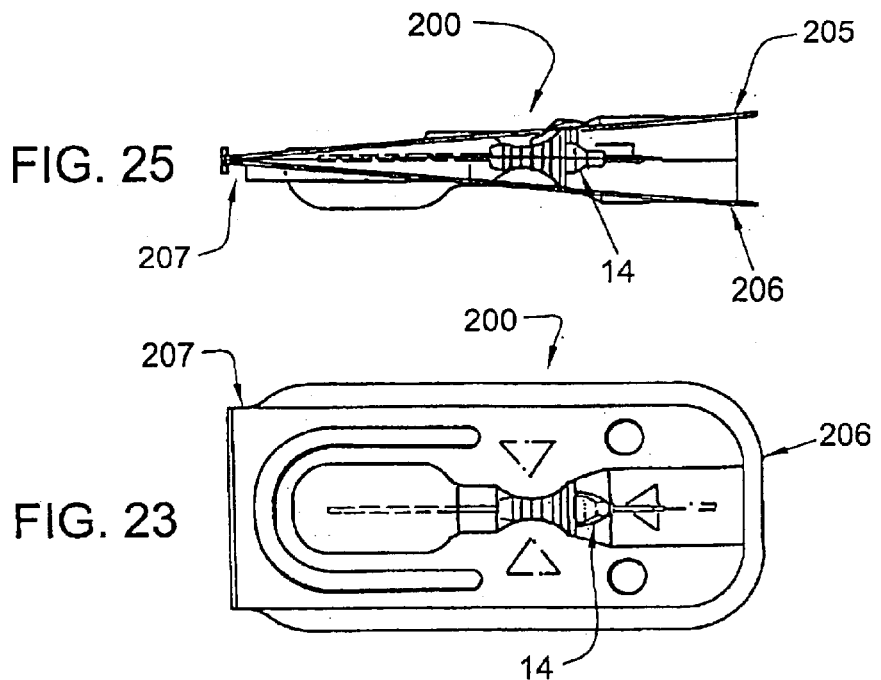
FIG. 25
FIG. 23
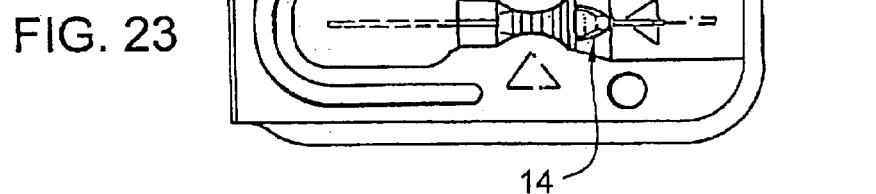
FIG. 24
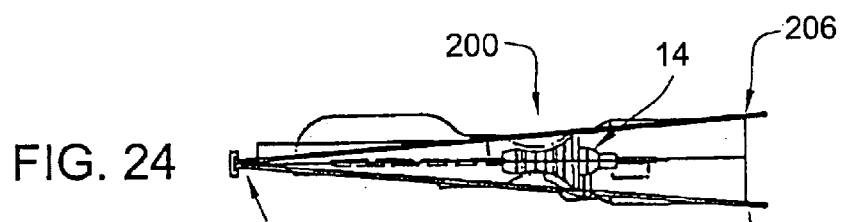
FIG. 22
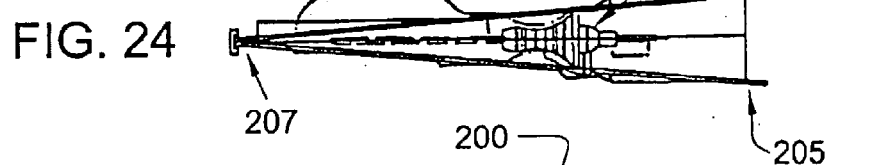
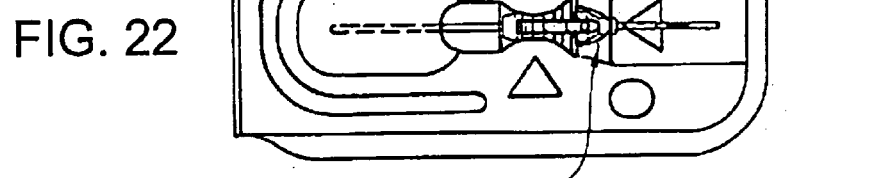
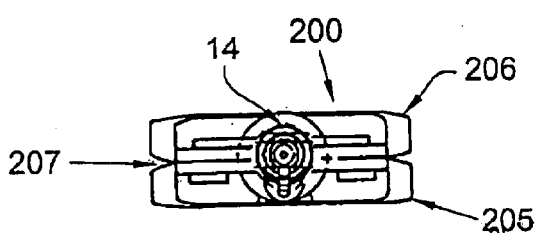
FIG. 26
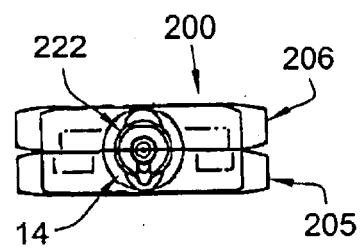
FIG. 27

PACKAGE FOR REMOVABLE DEVICE TIPS

CROSS-REFERENCE TO RELATED PATENT APPLICATIONS

This application is a divisional of prior U.S. patent application Ser. No. 09/661,892 filed Sep. 14, 2000 and now U.S. Pat. No. 6,478,030, which is a divisional of prior U.S. patent application Ser. No. 09/126,699 filed Jul. 30, 1998 and now U.S. Pat. No. 6,183,467 B1, which is a continuation-in-part of prior U.S. patent application Ser. No. 08/709,181 filed Sep. 6, 1996 and now U.S. Pat. No. 5,814,043, the entire disclosures of the foregoing patent applications being incorporated herein by reference.

BACKGROUND OF THE INVENTION

This invention relates to packages for surgical devices, and particularly to packages for removable tips of such devices.

Examples of surgical devices with removable tips include electrosurgical devices, such as monopolar cauterization devices and diathermy devices. Other types of removable tips are sharp tips (e.g., needles, pics, and blades) that are attached to the end of a handle.

SUMMARY OF THE INVENTION

This invention features a package for a surgical device tip which may be used for insertion of the tip onto and removal of the tip from the handle of the surgical device, without requiring any direct contact between the user's hand and the tip.

In one general aspect of the invention, a package for a tip of a surgical device capable of removable attachment to an end of a handle includes a housing having a tip cavity shaped to receive the tip and an opening through which the end of the handle is insertable for removable attachment to the tip. Related aspects of the invention feature the combination of the package and a tip disposed in the package, and methods of using the package to attach the tip onto, and detach the tip from, the handle.

Preferred embodiments may include one or more of the following features.

A releasable locking mechanism, which is released in response to the end of the handle being disposed in the opening for removable attachment to the tip, retains the tip in the tip cavity. The releasable locking mechanism is a movable protrusion of an inner surface of the housing which forms the cavity, and is movable by the end of the handle to release the tip.

The package is made from a single piece of molded material, which may be a clear plastic material such as co-polyester PETG or polyvinyl chloride. The package is made by molding, such as vacuum molding.

In another general aspect of the invention, the package includes a top portion, a bottom portion, and a hinging segment connecting the top portion and the bottom portion. The top portion and the bottom portion form a tip cavity when the top portion and the bottom portion are folded together along the hinging segment. The tip cavity is shaped to receive the tip and has an opening through which the end of the handle is insertable for removable attachment to the tip.

Preferred embodiments may also include one or more of the following features.

A releasable locking mechanism, including a releasable locking recess formed in the top portion and the bottom portion, holds the tip within the tip cavity. The locking mechanism is releasable in response to the end of the handle being disposed in the opening for removable attachment to the tip.

The tip includes a protrusion, and the top portion includes a positioning cavity shaped to receive the protrusion to prevent the tip from rotating within the tip cavity. The end of the handle has a bevel, and the locking mechanism has a ramp disposed adjacent to the locking recess so that the bevel contacts the ramp to release the locking mechanism.

The top and bottom portions include several molded features. For example, the top portion includes a molded pocket and the bottom portion includes a molded boss, the boss engaging the pocket to hold the top portion and the bottom portion together when folded along the hinging segment. The top and bottom portions also include interlocking ribs. The top portion includes a molded placement indicator to indicate placement of a user's fingers, and a molded directional indicator to indicate a direction of movement of the handle in the tip cavity.

In use, a tip disposed within the package is attached to the end of a handle by inserting the end of the handle into the package opening to release the tip, pushing the end of the handle inserted into the opening to attachably engage the tip to the end of the handle, and withdrawing the end of the handle from the opening with the attachably engaged tip. Similarly, the tip is detached from the handle and stored in the package by inserting the end of the handle with the removably attached tip into the package opening, pushing the end of the handle inserted into the opening until the tip is released and retained in the package, and withdrawing the end of the handle from the opening. Pressure may be applied to and released from the package to assist in the attachment of the tip onto and the removal of the tip from the handle.

The invention is particularly well-suited, but by no means limited, for use with bipolar electrosurgical devices with removable bipolar tips which can be easily and conveniently detached from the handle, such as the devices disclosed in the parent application.

Thus, in one embodiment, the tip is attachable to a handle having an opening and a plurality of coaxial, axially spaced electrical contacts. The tip includes a tip housing having a proximal end and a distal end, the proximal end of the tip housing configured to be received within the opening of the handle. A plurality of electrodes are disposed through the tip housing, the electrodes having distal ends that extend distally from the distal end of the tip housing and proximal ends that are coaxial and axially spaced from each other and that extend proximally from the proximal end of the tip housing for connection to the coaxial, axially spaced electrical contacts of the handle when the proximal end of the tip housing is inserted in the opening of the handle. The proximal end of the tip housing is constructed to be releasably secured to the handle (e.g., by a snap fit) for operation of the surgical device solely by inserting the proximal end of the tip housing axially into the opening of the handle. The package has a tip cavity shaped to receive the tip. In an alternative embodiment, the tip is a sharp tip.

In use, the user simply selects a packaged tip from an inventory of such tips, and installs the tip onto the device handle in the manner described above. The device is then ready for use in surgery. After it is used, the tip is removed from the handle and stored in the package, using the procedure described above, and discarded or stored for subsequent use during the same surgical procedure. If desired, another packaged tip may be selected, inserted onto the handle, and used to perform a different treatment (e.g., cauterization) during the same surgical procedure.

The package securely retains and protects each tip, thereby eliminating several safety and sterility concerns that accompany the use of removable surgical tips. Among other advantages, the package eliminates the need for the user's hand to contact the tips during either installation or removal of the tips. Use of the package prevents contamination or exposure by the user to used tips. Further, tips delivered in sterile packages can be attached to the handle without risking contamination from the user's hands.

The package allows for simple insertion of tips onto and removal of tips from the handle of the surgical device. The package may be shaped to accommodate various types of tips used with the handle. The package, which may permit the user to see the tip inside, allows for efficient organization of tips during a surgical procedure.

The package also protects the user from the sharp ends of the tips' electrodes. The interlocking ribs of the top and bottom portions and the hinging segment help to avoid accidental release of the tip retained in the package and to prevent the sharp end of the tip electrode from sliding out through the sides of the package. Also, the electrical contacts of the tip electrodes that attach to the handle are recessed in the opening of the housing to avoid accidental contact with the user's hands.

Other features and advantages of the invention will become apparent from the following description and from the claims.

BRIEF DESCRIPTION OF THE DRAWINGS

FIG. 9 is a top plan view of a package for a removable tip of a surgical device in an unfolded state.

FIG. 10 is a side view of the package of FIG. 9 in an unfolded state.

FIG. 11 is a side, partially cross-sectioned view of the package of FIG. 9, as folded, positioned to receive the surgical device including the tip inserted onto the handle.

FIG. 12 is a side, partially cross-sectioned view of the package of FIG. 9, as folded, receiving the tip of the surgical device inserted onto the handle.

FIG. 13 is a side, partially cross-sectioned view of the package of FIG. 9, as folded, retaining the tip of the surgical device which has been removed from the handle.

FIG. 22 is a top plan view of the tip and package of FIG. 21.

FIG. 23 is a bottom plan view of the tip and package of FIG. 21.

FIG. 24 is an elevational view of one side of the tip and package of FIG. 21.

FIG. 25 is an elevational view of the other side of the tip and package of FIG. 21.

FIG. 26 is a front elevational view of the tip and package of FIG. 21.

FIG. 27 is a rear elevational view of the tip and package of FIG. 21.

DESCRIPTION OF PREFERRED EMBODIMENTS

Figure 1:
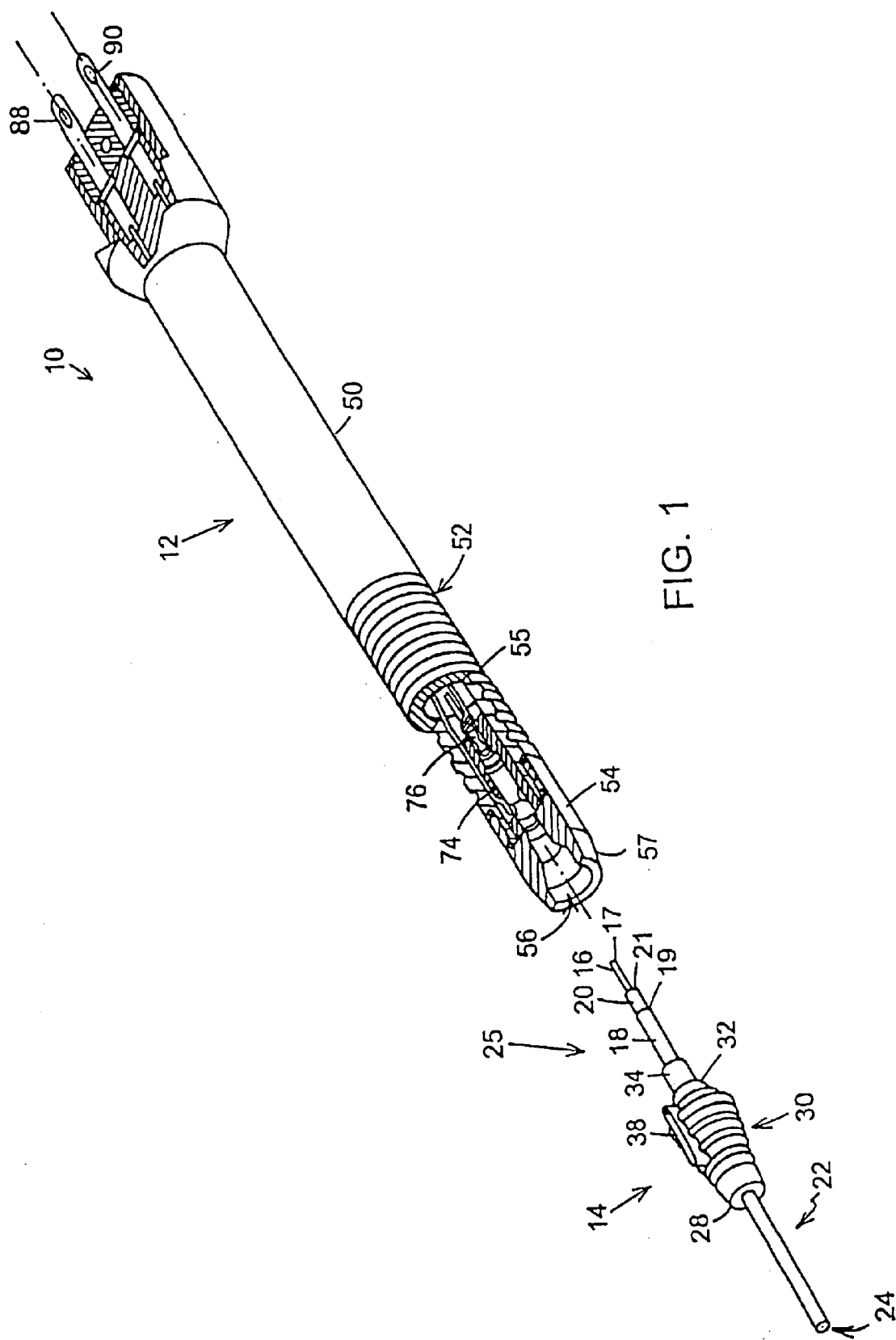
FIG. 1 is a perspective view of a surgical device with a tip of the device separated from a handle, and the handle partially cut away.
Figure 2:
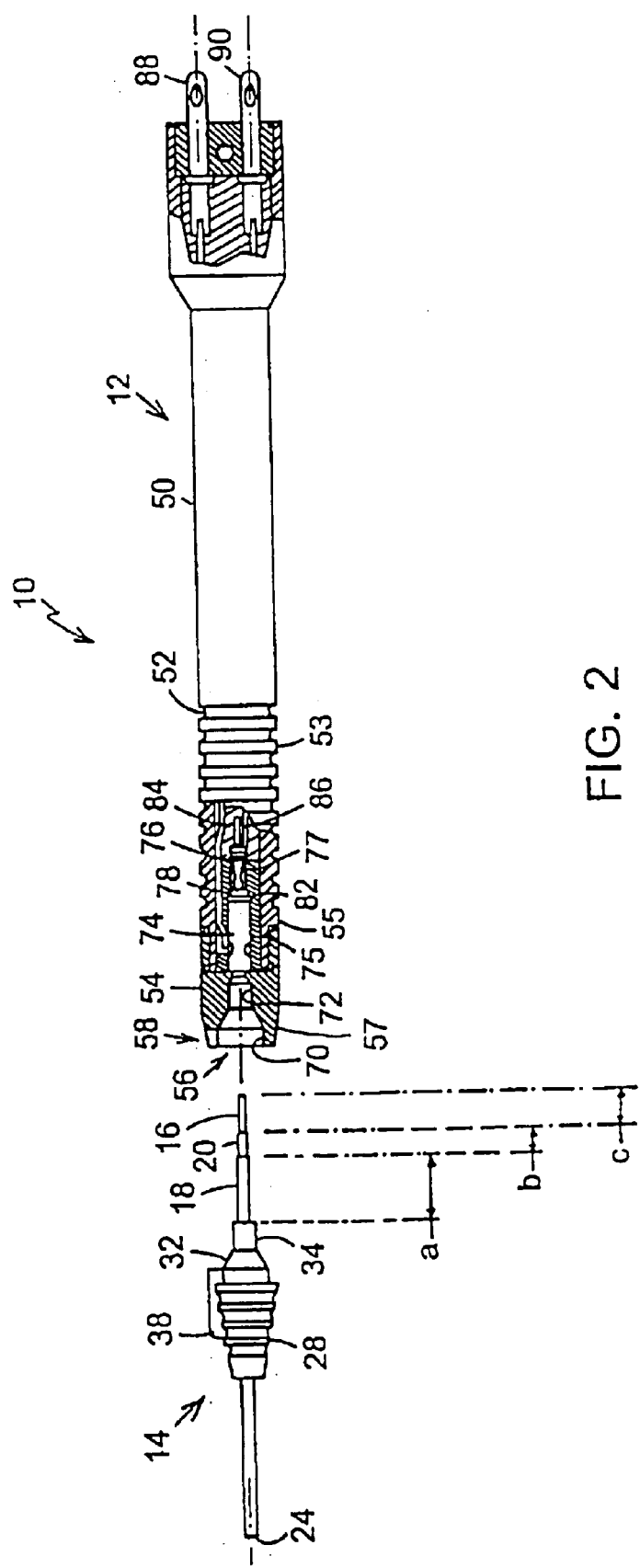
FIG. 2 is a side, partially cross-sectioned view of the tip and handle of FIG. 1.
Figure 3:
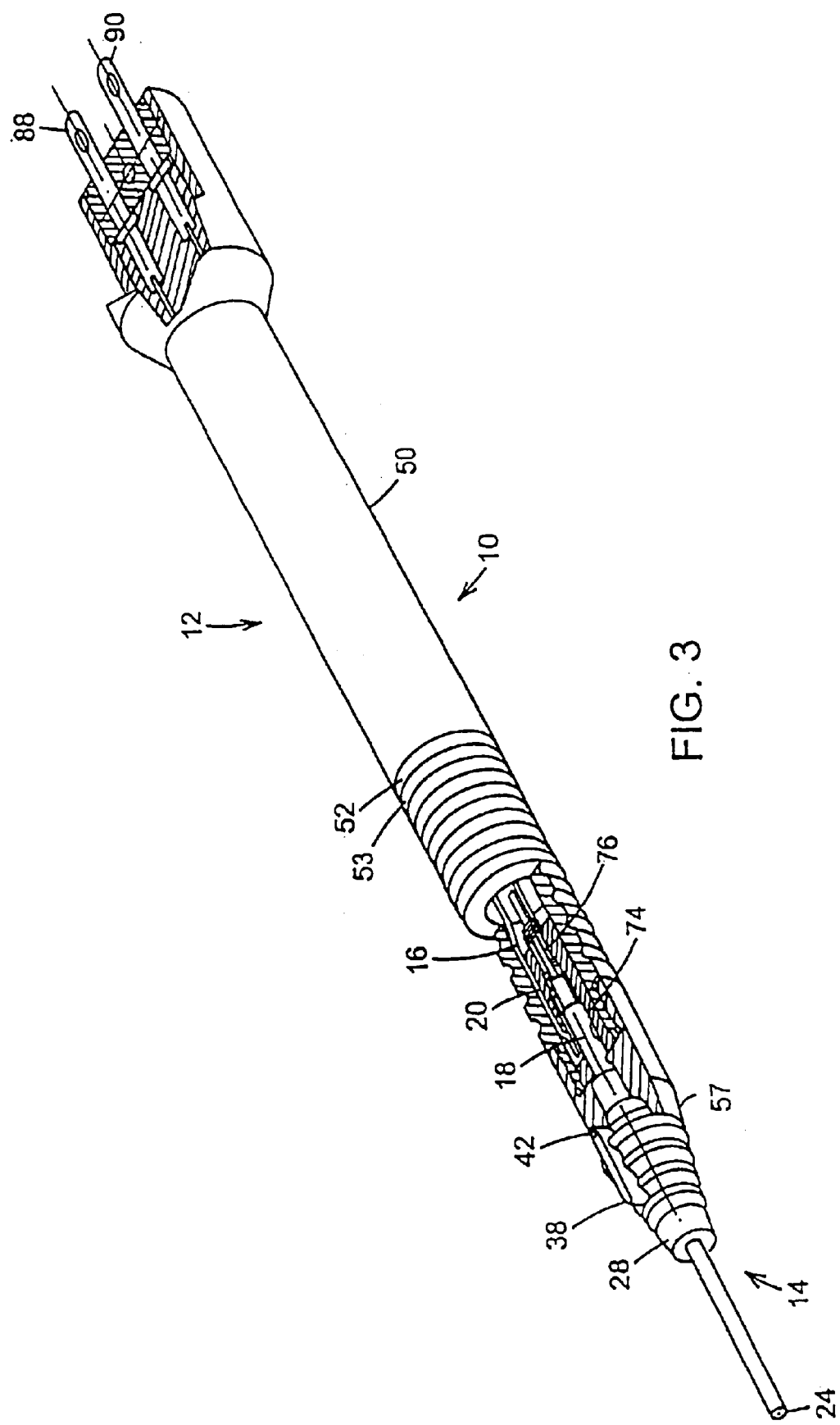
FIG. 3 is a perspective view of the surgical device of FIG. 1 with the tip inserted in the handle.
Figure 4:
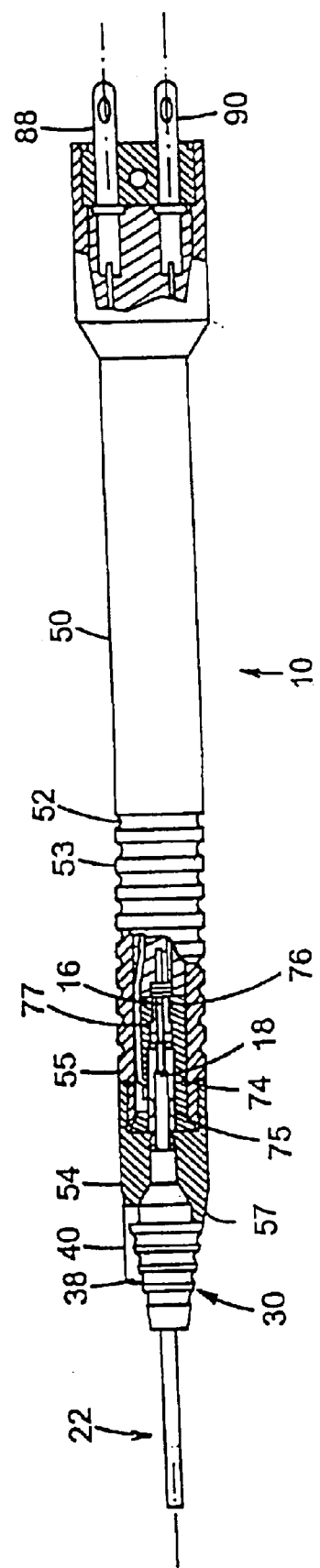
FIG. 4 is a side, partially cross-sectioned view of the device of FIG. 3.

Before describing the package of the present invention, it would be helpful to describe one kind of surgical instrument with which the package may be used. Referring to FIGS. 1 and 2, a surgical device 10 has a reusable handle 12 with a removable tip 14. In use, tip 14 is inserted into handle 12 as shown in FIGS. 3 and 4. After use, tip 14 is removed from handle 12, discarded, and a new tip is inserted into handle 12.

Tip 14 comprises a solid, cylindrical inner electrode 16 disposed coaxially inside a hollow, cylindrical outer electrode 18. Electrodes 16, 18 are closely spaced and separated by a thin coaxial insulator 20. Alternatively, tip 14 may be made by coating outer electrode 18 onto an insulated inner electrode 16, as described in the copending patent application of Harry Reimels et al. entitled "Bipolar Electrosurgical Instrument and Method for Making the Same," filed Jan. 26, 1996 as Ser. No. 08/591,953, assigned to the present assignee and incorporated herein by reference.

A distal treatment end 22 of the electrodes includes a flat surface 24 that is applied to tissue during surgery. A proximal connection end 25 of the electrodes is configured for connection to handle 12. Electrodes 16, 18 form a substantially straight line from connection end 25 to treatment end 22.

At connection end 25, a proximal end 17 of inner electrode 16 is axially displaced from a proximal end 19 of outer electrode 18. A proximal end 21 of insulator 20 is disposed intermediate the proximal ends 17, 19 of electrodes 16, 18. As a result, a length (a) of electrode 18, a length (b) of insulator 20 and a length (c) of electrode 16 are exposed (FIG. 2).

Handle 12 includes an opening 56 at one end. The end of handle 12 also has a sloped bevel 57, the width of which increases as the distance to opening 56 increases. Two cylindrical electrical contacts 74, 76 separated by cylindrical receptacle 78 are arranged coaxially in opening 56. Contact 74 has one end 82 abutting an end of receptacle 78. Another end of receptacle 78 is adjacent to an end of contact 76.

Contact 76 has a smaller radius than contact 74, and receptacle 78 has a radius intermediate those of contacts 74, 76.

The length of contact 74 matches the combined lengths of outer electrode 18 and insulator 20 at connection end 25 (i.e. length a+length b in FIG. 2). The length of receptacle 78 and contact 76 together equal the length (c) of electrode 16 exposed at tip end 25.

A ring-like conductor 75, 77 is disposed on the inside surface of each electrical contact 74, 76. The inner diameter of conductors 75, 77 is only slightly larger than the diameter of electrodes 18, 16, respectively. In addition, each contact 74, 76 is connected by a wire 84, 86 to a connector pin 88, 90 at a proximal end of handle 12. Pins 88, 90 are adapted for connection to a high frequency power source.

Tip 14 also includes a plastic housing 28 mounted around the exterior of electrode 18. Treatment end 22 and connection end 25 of electrodes 16, 18 extend distally and proximally, respectively, from housing 28. The distal end of housing 28 is conically shaped and has a sloping, grooved exterior surface 30. A proximal end of housing 14 comprises a conical section 32 that terminates in a cylindrically-shaped nose 34. The shape of handle opening 56 is complementary to that of the proximal end of housing 28 so that housing 28 snugly mates with handle 12. Thus, the distal end of opening 56 includes a conically-shaped inner surface 70 that meets a cylindrically-shaped inner surface 72.

Handle 12 is formed as a cylindrical body 50 (made from, e.g. metal or composite material) with a distal section 54 that is threaded onto a proximal section 55. Opening 56 is disposed in distal section 54, while proximal section 55 includes the electrical contacts 74, 76, receptacle 78, wires 82, 86 and pins 88, 90. A series of grooves 52 is formed in the exterior surface of proximal section 55 to define a set of raised circumferential ribs 53 that assist the user in gripping the device.

Figure 5:
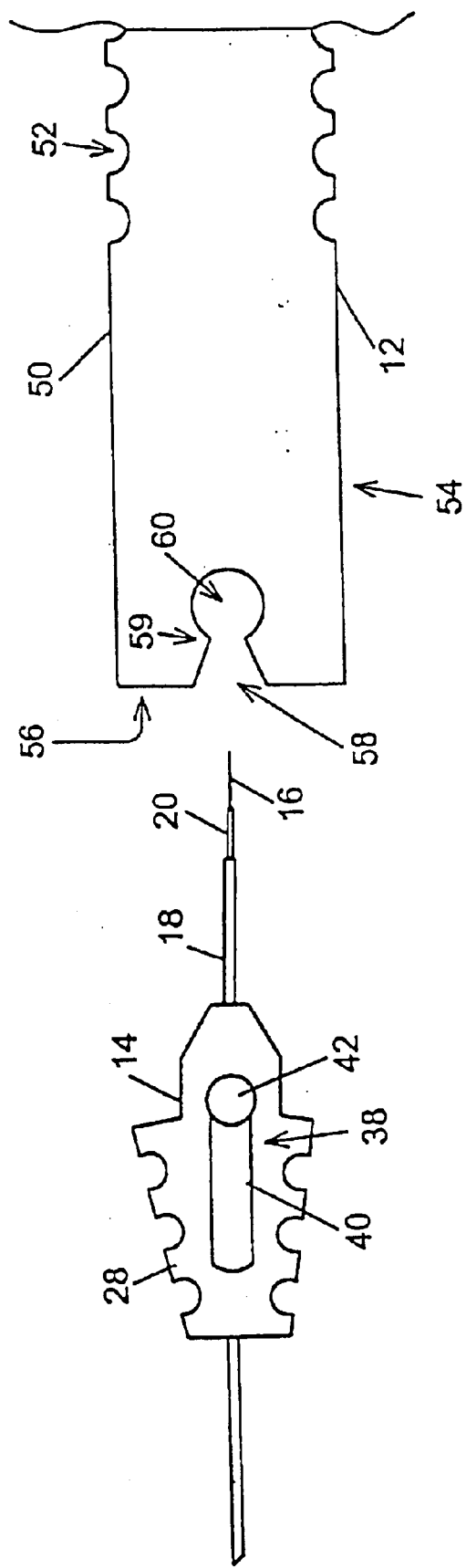
FIG. 5 is an enlarged view of the tip and handle of FIG. 1.
Figure 6A:
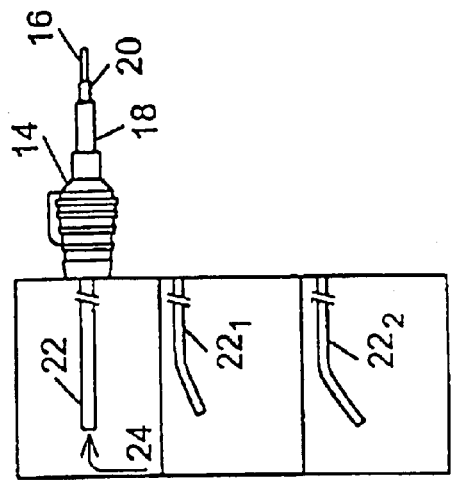
FIGS. 6A–6E show a variety of tips for use with the handle of FIG. 1.
Figure 6B:
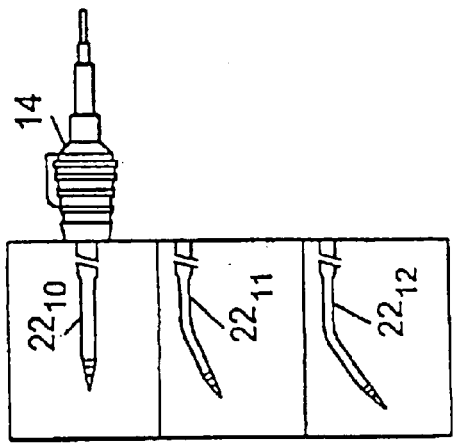
Figure 6C:
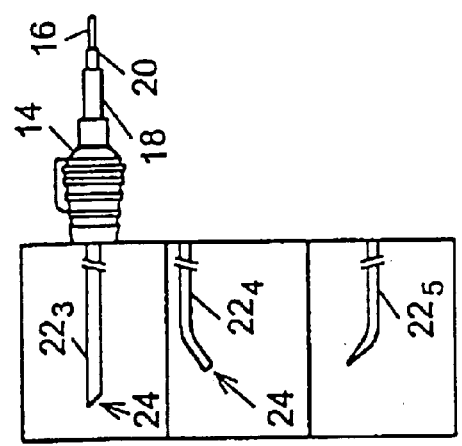
Figure 6D:
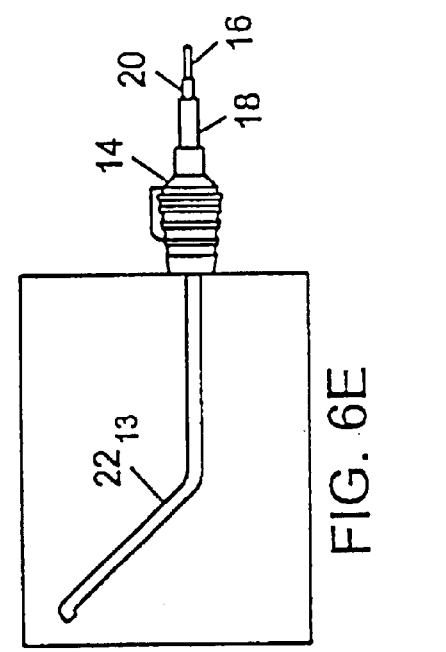
Figure 6E:
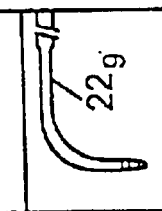

Referring also to FIG. 5, tip 14 includes a protrusion 38 extending from grooved surface 30 to an edge of tapered section 32, at a predetermined radial position with respect to electrodes 16, 18. Protrusion 38 has an axially-extending rectangular tab 40 that terminates proximally in a round button 42. The diameter of button 42 is slightly larger than the width of tab 40.

Distal end 54 of handle 14 includes an axially-extending, tapered slot 58 that communicates with opening 56. The proximal end 59 of slot 58 meets a round opening 60 that is only slightly larger than button 42 on tip 14. The diameter of round opening 60 slightly exceeds the width of slot 58 at end 59.

FIGS. 6A–6E show an inventory of tips 14 compatible with handle 12. Treatment ends 22 of tips 14 have a variety of configurations. For example, some tips 14 have treatment ends with a flat distal surface 24 (e.g, treatment end 22) which may be beveled (e.g., treatment end $22_3$), while others tips 14 have a concave distal surface 24 (e.g., end $22_4$). Still other tips 14 in the inventory have treatment ends that are tapered to a fine point (e.g., treatment end $22_{10}$), to a round, blunt distal surface 24 (e.g., treatment end $22_6$) or to a flat surface (e.g., end $22_5$). The treatment ends of some tips form a straight line from housing 28 to surface 24 (e.g., end 22), while others include a bend of 30°, 45°, or 90° (e.g., ends $22_7$, $22_6$, $22_9$, respectively). Another type of tip 14 includes a treatment end $22_{13}$ with two bends, appropriate for performing a capsulotomy.

In operation, a user selects a tip 14 from the inventory and inserts the selected tip 14 into handle 12 simply by aligning protrusion 38 on housing 28 with slot 58 in handle 12 and inserting connection end 25 of tip 14 into handle opening 56. The proximal end of housing 12 enters handle opening 56, and protrusion 38 slides into slot 58. As button 42 of protrusion 38 enters round opening 60, end 59 of slot 58 expands. After tip 14 is fully inserted, end 59 of slot 58 snaps back to its original size to hold button 42 firmly in opening 60. The exterior surfaces of housing sections 32, 34 also frictionally engage inner surfaces 70, 72 of opening 56. Tip 14 is thus held in handle 12 by a friction fit as well as by a snap fit.

As tip 14 is being inserted, outer electrode 18 and insulator 20 enter contact 76, and outer electrode 18 firmly contacts conductor 75. Similarly, inner electrode 16 slides into contact 74 and receptacle 78, and proximal end 17 of electrode 16 engages conductor 77. Friction between the adjacent surfaces of electrodes 16, 18 and conductors 77, 75 provides a reliable, secure electrical connection, and also helps avoid tip 14 disengaging from handle 12.

Figure 7:
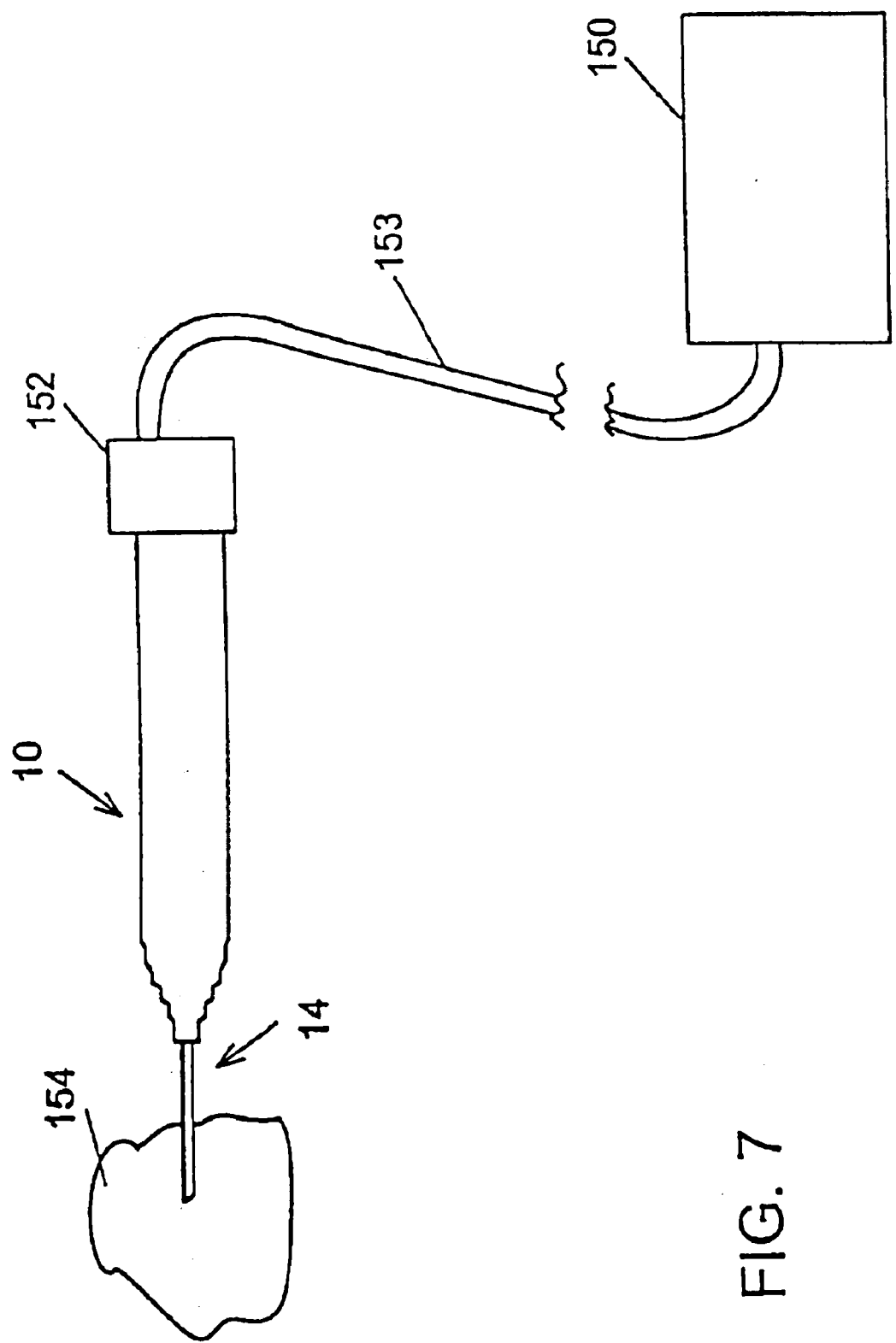
FIG. 7 is a schematic representation of the surgical device of FIG. 1 in use.

Referring to FIG. 7, the user connects device 10 to a high frequency power source 150 by connecting a standard socket 152 on a cable 153 to connector pins 88, 90. Power source 150 provides electrical power to contacts 74, 76 via pins 88, 90, which in turn provide the power to electrodes 16, 18 (FIG. 1). Holding body 50 of handle 12 and housing 28 of tip 14, the user places surface 24 of electrodes 16, 18 on tissue 154 to be treated, e.g., within the eye. The voltage applied by electrodes 16, 18 induces a high frequency current in the tissue, thereby performing cauterization, coagulation, or other surgical operations.

After use, the user detaches tip 14 from handle 12 by pulling tip 14 axially out of opening 56. Protrusion 38 on tip 14 forces edges 59 of slot 58 outward as button 42 is pulled through slot 58. The user discards tip 14, and sterilizes handle 12 (e.g., by autoclaving) for subsequent use.

The user then selects a new tip from the inventory of tips. For example, the user may choose tip 14 with treatment end $22_1$ shown in FIG. 7. The user then inserts the new tip in handle 12, as described above, and performs a new surgical procedure.

Alternatively, the user may sterilize and reuse tip 14 instead of discarding tip 14 after a single use. In this case, tip 14 would be made from reusable material capable of, e.g., withstanding autoclaving.

Proximal section 55 and distal section 54 of handle 12 may also be combined into a unitary, molded body.

Figure 8:
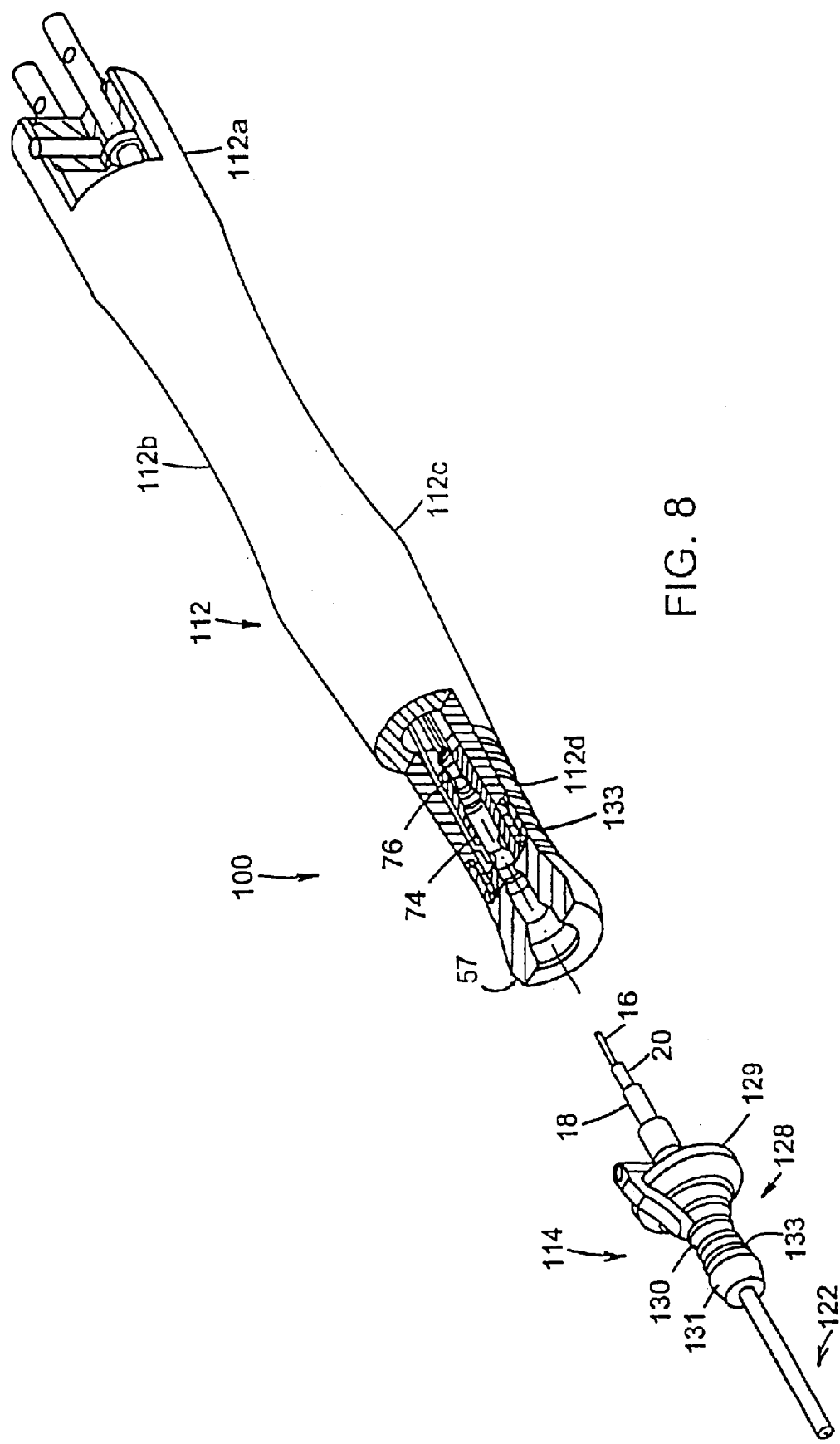
FIG. 8 shows another embodiment of a surgical device and removable tip.
Figure 21:
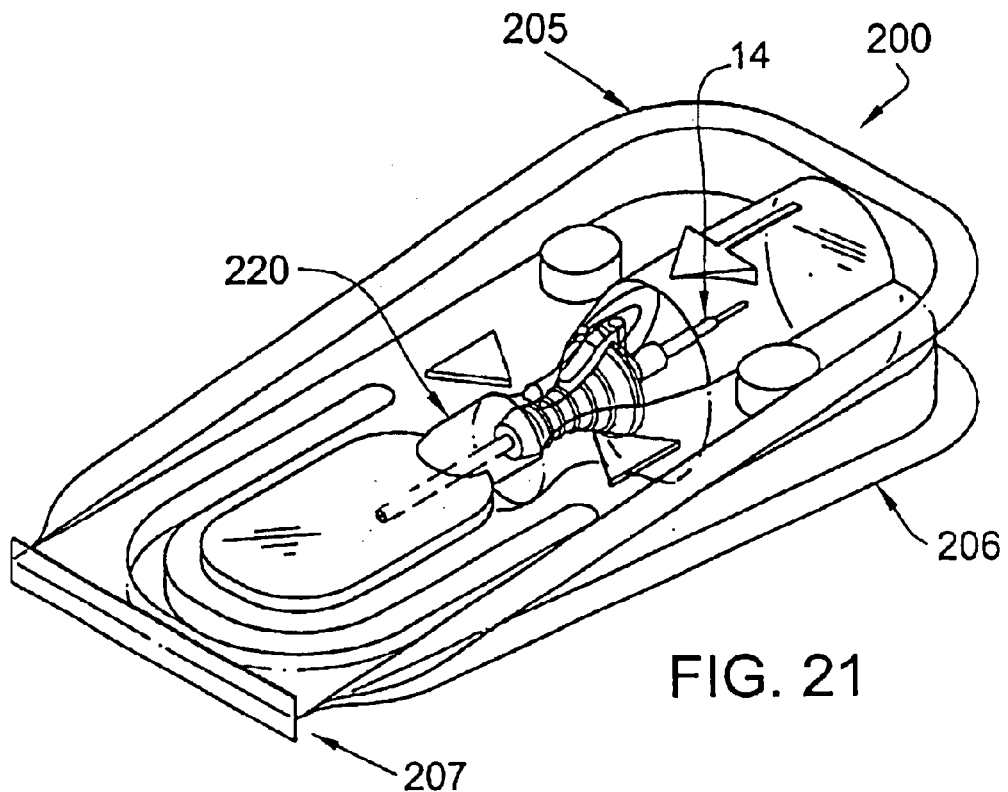
FIG. 21 is a perspective view of the package of FIG. 9, as folded, including the tip.
Figure 14:
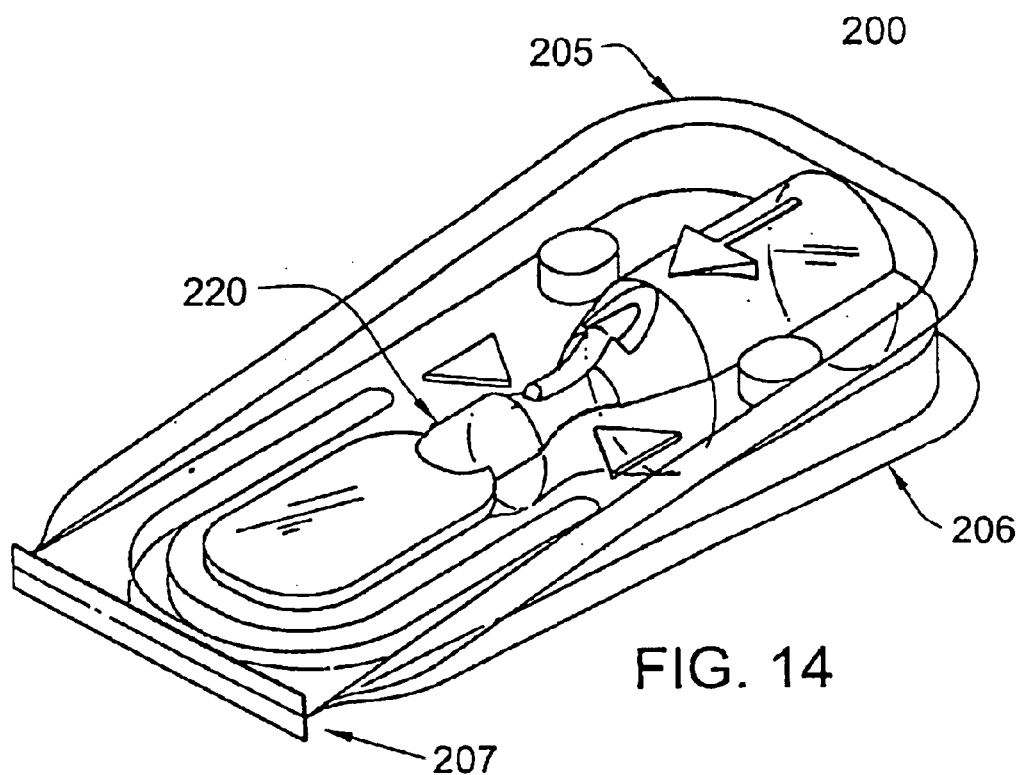
FIG. 14 is a perspective view of the package of FIG. 9, as folded.
Figure 18:
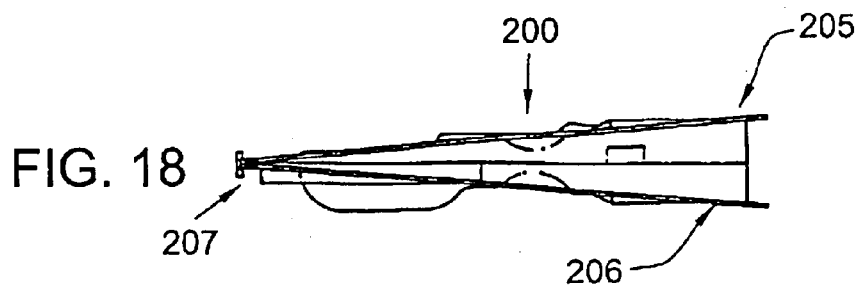
FIG. 18 is an elevational view of the other side of the package of FIG. 14.
Figure 16:
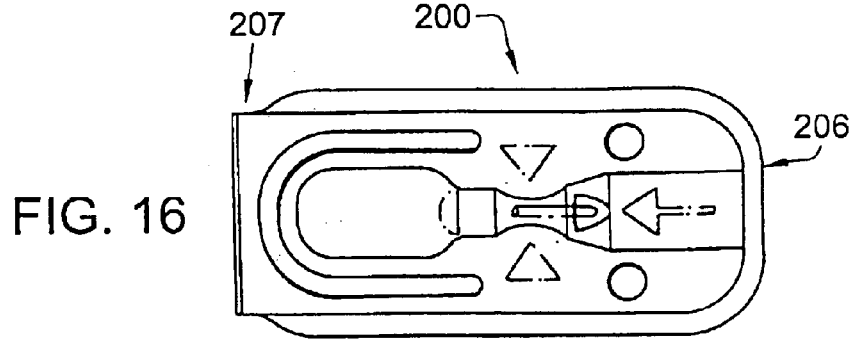
FIG. 16 is a bottom plan view of the package of FIG. 14.
Figure 17:
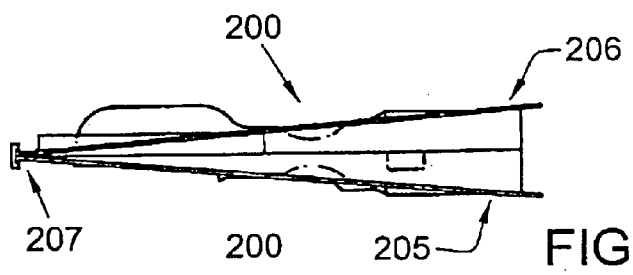
FIG. 17 is an elevational view of one side of the package of FIG. 14.
Figure 15:
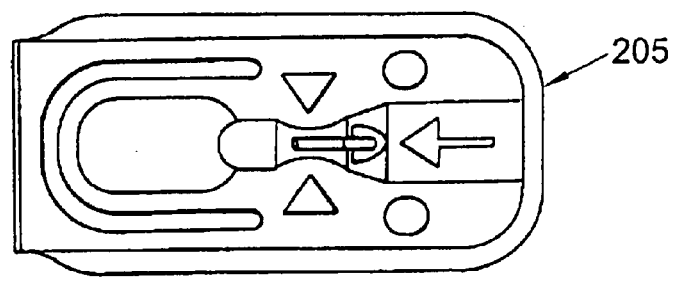
FIG. 15 is a top plan view of the package of FIG. 14.
Figure 19:
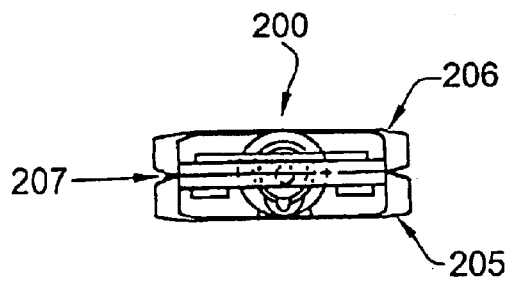
FIG. 19 is a front elevational view of the package of FIG. 14.
Figure 20:
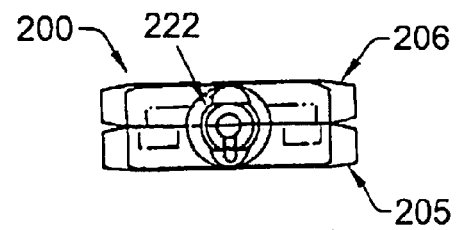
FIG. 20 is a rear elevational view of the package of FIG. 14.

The handle and tip may have other shapes. For example, referring to FIG. 8, surgical device 100 has a non-cylindrical handle 112 that axially tapers between relatively large diameter regions 112a, 112c and smaller waist regions 112b, 112d. This contoured shape fits comfortably in the user's hand. In particular, narrow waist region 112d can be gripped between the user's fingers to assist in precisely treatment end 122 of tip 114 in the body.

The housing 128 of tip 114 is hourglass-shaped, tapering from a relatively wide proximal region 129 to a narrow intermediate waist 130, and then to a somewhat larger-diameter distal region 131. With this shape, housing 128 fits securely in the user's hand (with waist 130 being gripped between the user's fingers) when inserting tip 114 into and removing tip 114 from handle 112. Both handle 112 and tip housing 128 may be ribbed 133 to further enhance gripping.

Referring to FIGS. 9–27, tip 14 (or tip 114) may be delivered in a reinforced, sterile "blister" package 200 which allows for easy insertion of the tip onto handle 12 and removal of the tip from the handle, without any direct contact between the user's hand and the tip. Package 200 can be sterilized and sealed within a sterile pouch (not shown) for use during surgery. Package 200 containing tip 14 may also be sterilized after insertion in the sterile pouch preferably using ethylene oxide (ETO) or gamma rays.

Package 200 is made from a single piece of thin, flexible plastic material, preferably 0.015 inch thick Kodak "Kodar" 6763 clear co-polyester medical PETG. Another material that may be used for package 200 is polyvinyl chloride. Package 200 is preferably made by vacuum molding the plastic material. Other methods of making package 200 include injection molding and pressure or vacuum thermoforming of the plastic material.

Referring to FIGS. 9–11, package 200 includes a top portion 205 and a bottom portion 206 connected by a rigid hinging segment 207. Hinging segment 207 includes two hinging points 207a which create a blunt shelf 207b, and two walls 207c which provide rigidity for the hinging segment. Package 200 is folded into a closed position by folding top portion 205 and bottom portion 206 toward each other along hinging segment 207, and forming the hinging segment itself by folding along hinging points 207a. FIGS. 9 and 10 show package 200 prior to folding, and FIGS. 11–14 show the package with the top and bottom portions folded together.

Referring to FIGS. 11–14, when package 200 is folded together, molded top portion 205 and molded bottom portion 206 form a cavity 220 shaped to receive the entire tip 14. Top portion 205 and bottom portion 206 both include flat surfaces 262 and 264 that substantially meet each other when package 200 is folded together. Cavity 220 may be shaped to accept, discharge and protect all types of shapes of tips that are used with handle 12 (e.g., the tips shown in FIGS. 6A–6E). Cavity 220 includes an upper chamber 224 and a lower chamber 226. Cavity 220 is also shaped to receive the conically shaped housing 28 of tip 14, including sloping, grooved exterior surface 30. Cavity 220 has an opening 222 into lower chamber 226 that is large enough only to receive the end of handle 12 for inserting tip 14 onto and removing the tip from the handle. The electrical contacts of the tip electrodes which extend from tip 14 and attach to handle 12 are recessed within opening 222 to avoid accidental contact with the user's hands.

Upper chamber 224 is formed by molded sections 208 and 209 in top portion 205 and bottom portion 206, respectively, when the top and bottom portions are folded toward each other. Upper chamber 224 is large enough to accommodate the electrodes of both straight and bent tips, such as the tips shown in FIGS. 6A–6E.

Housing 28 of tip 14 is securely held and properly oriented in package 200 within lower chamber 226. Lower chamber 226 includes positioning cavity 201 and a releasable locking mechanism, which includes locking recesses 202, 202a and ramps 203, 203a adjacent to the locking recesses. Positioning cavity 201 is shaped to receive tab 40 and button 42 of protrusion 30 on tip 14. Positioning cavity 201 prevents tip 14 from rotating about central axis 260 within cavity 220. Positioning cavity 201 also prevents damage to the electrodes of tip 14 by restraining the tip from being pushed too far forward into upper chamber 224.

Tip 14 is rearwardly retained within cavity 220 by locking recesses 202, 202a. Locking recesses 202, 202a protrude into the path of movement of tip 14 along central axis 260 to hold the tip in place and prevent the tip from sliding out of opening 222. Locking recesses 202, 202a can be separated slightly radially outward from central axis 260 by pushing against ramps 203, 203a to release tip 14 from cavity 220.

Top portion 205 includes molded pockets 210, and bottom portion 206 includes corresponding molded interlocking bosses 211. Pockets 210 and bosses 211 are positioned so that when top portion 205 and bottom portion 206 are folded toward each other, the bosses engage the pockets. Bosses 211 are shaped so that they fit snugly into and are frictionally held within corresponding pockets 210 when the bosses are firmly pushed into the pockets. The combination of pockets 210 and bosses 211, as well as rigid hinging segment 207, helps to maintain package 200 in a closed position during shipping and usage, but allows the package to be opened manually if necessary.

Top portion 205 and bottom portion 206 also contain interlocking horseshoe-shaped ribs 248 and 250, respectively, which provide additional rigidity to package 200. Ribs 248 and 250 also provide a 4-layer barrier between cavity 220 and the package exterior to help to avoid accidental release of the tip retained in the package and to prevent the sharp end of the tip electrode from sliding out through the sides of package 200. As with pockets 210 and bosses 211, ribs 248 and 250 are positioned so that when top portion 205 and bottom portion 206 are folded together the ribs engage each other, and the ribs are shaped so that one of the ribs fits snugly into and is frictionally held within corresponding the rib. Hinging segment 207 and ribs 248 and 250 prevent accidental opening of package 200 during insertion of tip 14 onto and removal of the tip from handle 12, which helps to avoid contact between the tip and the user's hand.

Double arrows 242 molded into top portion 205 indicate the location for proper placement of the user's fingers to grasp package 200 during insertion of tip 14 onto and removal of the tip from handle 12. Single directional arrow 244 molded onto the top portion 205 of package 200 indicates the direction of handle movement and ensures correct alignment between handle 12 and tip 14 during insertion and removal. Top portion 205 may also contain a labeling area 246, in which a message or text is molded into the plastic, preferably by hot stamping.

Referring to FIGS. 11–13, package 200 is used to insert tip 14 onto and to remove the tip from handle 12 without direct contact between the tip and the user's hand. To insert tip 14 onto handle 12, the user firmly grasps package 200 between double arrows 242 and pushes the end of the handle into opening 222 along the direction of single directional arrow 244. When the end of handle 12 is pushed into package 200 through opening 222, bevel 57 of handle 12 urges locking recesses 202, 202a radially outward and away from tip housing 28 by pushing against ramps 203, 203a, thus releasing tip 14 from lower chamber 226. Handle 12 is pushed into cavity 220 until tip 14 is fully inserted onto the handle. The interface between tip 14 and handle 12 prevents locking recesses 202, 202a from recapturing tip housing 28 during withdrawal of the handle from package 200 with the fully inserted tip.

To remove inserted tip 14 from package 200, the user releases the tension placed on the package between double arrows 242 and withdraws handle 12 in the direction opposite to single directional arrow 244. The retention of tip 14 on handle 12 is sufficient to keep tip 14 fully inserted on handle 12 during withdrawal from package 200 and during use in a surgical procedure, but allows for ease of removal of tip 14 from handle 12 with or without the use of package 200.

Package 200 may also be used to remove an inserted tip 14 from handle 12. The user pushes handle 12 with inserted tip 14 into opening 222 in the direction of arrow 244, making sure that protrusion 30 of tip 14 is aligned to slide into positioning cavity 201. As the user pushes handle 12 through opening 222 and tip 14 enters cavity 220, bevel 57 of handle 12 contacts ramps 203, 203a to urge locking recesses 202, 202a radially outward from central axis 260, allowing tip 14 to fully enter cavity 220. The user then grasps package 200 between double arrows 242 with his or her fingers to apply pressure to hold tip 14 within cavity 220. Tip 14 is then separated from handle 12 by pulling the handle away from the tip. As the user withdraws handle 12 from opening 222, the interface between tip 14 and handle 12 separates, and handle 12 moves down ramps 203, 203a allowing locking recesses 202, 202a to recede radially inward toward central axis 260 and recapture tip 14. Tip 14, securely held within its package 200, may then be discarded or stored for subsequent use during the same surgical procedure.

The use of package 200 for each tip provides the user with efficient access to a variety of different tips during surgery. Since a tip may be used several times for the same patient during a single surgical procedure, the tips used with the patient may be efficiently stored in their packages during the surgical procedure, without contamination due to handling by the user. The return of the tips to their packages during a surgical procedure allows for minimal disposal and waste of tips. Further, by placing each tip into its package after it is used during a surgical procedure, a variety of tips used with a single handle during the surgical procedure may be efficiently organized.

Moreover, package 200 allows the user to remove used tips from the handle in a simple fashion and without direct contact between the tips and the user's hand. Thus, patient-contaminated tips may be safely manipulated and stored during surgery and disposed of after surgery. In particular, use of the package to insert tips onto and remove tips from the handle decreases the risk of puncturing hazardous waste bags and infecting the user or clinical staff.

Other embodiments are within the following claims. For example, the package can also be used with monopolar, diathermized and non-bipolar tips, as well as other sharp tips such as cannulae, pics and blades, that are removably attachable to a handle.

What is claimed is:

1. A package for a tip of a surgical device capable of removable attachment to and detachment from an end of a handle, comprising
   a housing comprising a top portion, a bottom portion, and a hinging segment connecting said top portion and said bottom portion, said top portion and said bottom portion forming a tip cavity when the top portion and said bottom portion are folded together along said hinging segment, said tip cavity being shaped to receive the tip and said housing having an opening through which the end of the handle is insertable and withdrawable for both removable attachment to the end of the handle to the tip received in said tip cavity and subsequent detachment of the tip from the end of the handle.

2. The package of claim 1 further comprising a releasable locking mechanism for retaining the tip in the tip cavity, said locking mechanism being released in response to the end of the handle being inserted in said opening.

3. The package of claim 2 wherein said releasable locking mechanism includes a movable protrusion of an inner surface of said housing which forms said cavity, said protrusion being movable by the end of the handle to release said locking mechanism.

4. The package of claim 2 wherein said releasable locking mechanism comprises a releasable locking recess formed in said top portion and said bottom portion to hold the tip within said tip cavity.

5. The package of claim 4 wherein said locking mechanism further comprises a ramp disposed adjacent said locking recess of being contacts by a bevel on the end of the handle to release the locking mechanism.

6. The package of claim 1 wherein said housing is made from a single piece of molded material.

7. The package of claim 6 wherein said material is plastic.

8. The package of claim 6 wherein said material is co-polyester PETG.

9. The package of claim 6 wherein said material is polyvinyl chloride.

10. The package of claim 6 wherein said housing is made by vacuum molding.

11. The package of claim 6 wherein said material is clear.

12. The package of claim 1 wherein said top portion includes a positioning cavity shaped to received a protrusion on the tip, said positioning cavity preventing the tip from rotating within the tip cavity.

13. The package of claim 1 wherein said top portion, said bottom portion and said hinging segment are made from a single piece of molded plastic material.

14. The package of claim 13 wherein said top portion includes a molded pocket and said bottom portion includes a molded boss, said boss engaging said pocket to hold said top portion and said bottom portion together when folded along said hinging segment.

15. The package of claim 13 wherein said top portion and said bottom portion include interlocking ribs.

16. The package of claim 13 wherein said top portion includes a molded placement indicator to indicate placement of a user's fingers.

17. The package of claim 13 wherein said top portion includes a molded directional indicator to indicate a direction of movement of the handle in said tip cavity.

18. A package for a tip of a surgical device capable of removable attachment to an end of a handle, comprising
   a housing having a tip cavity shaped to receive the tip, an opening through which the end of the handle is insertable for removable attachment of the end of the handle to the tip received in said tip cavity, and a pair of opposed locking members formed by said housing and releasably retaining the tip in said tip cavity, said locking members being movable radially outwardly of a central axis of said tip cavity in response to insertion of the end of the handle in said opening to release the tip from said tip cavity.

19. The package recited in claim 18 wherein said opposed locking members comprise a pair of opposed locking protrusions formed by recesses in said housing, said locking protrusions protruding into the path of movement of the tip along said central axis of said tip cavity.

20. The package recited in claim 19 and further including a pair of ramps on said housing adjacent said recesses, respectively, for being pushed against by the end of the handle inserted in said opening to move said locking members radially outwardly of said central axis.

21. The package recited in claim 18 and further including indicia on said housing indicative of a location at which grasping pressure is to be applied to said housing during removable attachment of the end of the handle to the tip received in said tip cavity.

22. The package recited in claim 21 wherein said indicia includes a pair of arrows to indicate grasping of said housing at said arrows.

23. The package recited in claim 22 wherein said arrows are located on opposite sides of said tip cavity.

24. A package for a tip of a surgical device capable of removable attachment to an end of a handle, comprising a housing having a tip cavity shaped to receive the tip and an opening through which the end of the handle is insertable for removable attachment of the end of the handle to the tip received in said tip cavity, said tip cavity including a central axis and a positioning cavity extending radial to said central axis for receiving a protrusion of the tip; and indicia on said housing longitudinally aligned with said positioning cavity, said indicia being alignable with a slot in the end of the handle inserted in said opening to align the slot with said positioning cavity.

25. The package recited in claim 24 wherein said indicia indicates a direction of insertion for the end of the handle in said opening.

26. The package recited in claim 25 wherein said indicia includes an arrow.

* * * * *